United States Patent
Park et al.

(10) Patent No.: US 8,114,018 B2
(45) Date of Patent: Feb. 14, 2012

(54) ADJUSTABLE LINE AND NET RETRACTORS

(76) Inventors: Adrian E. Park, Crownsville, MD (US); Charles F. Knapp, Georgetown, KY (US)

(*) Notice: Subject to any disclaimer, the term of this patent is extended or adjusted under 35 U.S.C. 154(b) by 221 days.

(21) Appl. No.: 12/087,559

(22) PCT Filed: Oct. 10, 2007

(86) PCT No.: PCT/US2007/080948
§ 371 (c)(1),
(2), (4) Date: Nov. 5, 2008

(87) PCT Pub. No.: WO2008/045940
PCT Pub. Date: Apr. 17, 2008

(65) Prior Publication Data
US 2009/0198107 A1 Aug. 6, 2009

Related U.S. Application Data

(60) Provisional application No. 60/850,496, filed on Oct. 10, 2006, provisional application No. 60/850,708, filed on Oct. 10, 2006.

(51) Int. Cl.
*A61B 1/32* (2006.01)
(52) U.S. Cl. ......... 600/215; 600/206; 600/217; 600/235
(58) Field of Classification Search .................. 600/201, 600/203, 204, 206, 209, 210, 215, 217, 219, 600/235
See application file for complete search history.

(56) References Cited

U.S. PATENT DOCUMENTS

| | | | | |
|---|---|---|---|---|
| 5,307,790 | A | * | 5/1994 | Byrne ........................... 600/206 |
| 5,415,666 | A | | 5/1995 | Gourlay et al. |
| 5,582,577 | A | * | 12/1996 | Lund et al. .................... 600/204 |
| 5,634,882 | A | | 6/1997 | Gagner |
| 5,716,326 | A | | 2/1998 | Dannan |
| 5,885,271 | A | | 3/1999 | Hamilton et al. |
| 5,921,979 | A | | 7/1999 | Kovac et al. |
| 5,964,698 | A | * | 10/1999 | Fowler .......................... 600/217 |
| 5,972,022 | A | * | 10/1999 | Huxel ........................... 606/215 |
| 6,206,827 | B1 | | 3/2001 | Chin et al. |
| 6,358,196 | B1 | | 3/2002 | Rayman |

(Continued)

FOREIGN PATENT DOCUMENTS

WO WO 2008-090978 A1 7/2008

(Continued)

OTHER PUBLICATIONS

International Search Report dated May 24, 2010.

*Primary Examiner* — Eduardo C Robert
*Assistant Examiner* — Ellen C Hammond
(74) *Attorney, Agent, or Firm* — Scott D. Wofsy; Edwards Wildman Palmer LLP (57) ABSTRACT

Devices for use during surgical or non-surgical procedures can move items from the field of view or work space. Retraction of items during any surgical or non-surgical procedure moves the items from the field of view or work space. The flexibility and compactness of a retraction device can make it suitable for surgery, especially minimally invasive surgery (MIS).

7 Claims, 9 Drawing Sheets

U.S. PATENT DOCUMENTS

| | | |
|---|---|---|
| 6,824,511 B1 | 11/2004 | Bell et al. |
| 7,018,332 B1 * | 3/2006 | Masson et al. ................. 600/227 |
| 7,112,172 B2 | 9/2006 | Orban, III et al. |
| 2003/0009080 A1 | 1/2003 | Peng et al. |
| 2006/0149135 A1 | 7/2006 | Paz |
| 2007/0088390 A1 | 4/2007 | Paz et al. |
| 2007/0250116 A1 * | 10/2007 | Raju ............................. 606/216 |
| 2007/0282355 A1 | 12/2007 | Brown et al. |
| 2008/0114377 A1 | 5/2008 | Shibata |
| 2008/0140218 A1 * | 6/2008 | Staskin et al. ............. 623/23.72 |
| 2010/0204727 A1 * | 8/2010 | Dominguez .................. 606/205 |

FOREIGN PATENT DOCUMENTS

WO    WO 2006-098994 A1    9/2008

* cited by examiner

Fig. 1

Case A

Case B

Length A

Length B

ADJUSTABLE LINE AND NET RETRACTORS

CLAIM OF PRIORITY

This application claims priority to U.S. Provisional Patent Application Ser. No. 60/850,496, filed Oct. 10, 2006, and U.S. Provisional Patent Application Ser. No. 60/850,708, filed Oct. 10, 2006, each of which is incorporated by reference in its entirety.

TECHNICAL FIELD

The invention relates to devices for use during surgical or non-surgical procedures in order to move items from the field of view or work space.

BACKGROUND

Surgical procedures can require the retraction of tissue sections, tissue flaps, organs, organ flaps and the like so the field of view or work area is clear. For example, a segment of the liver may need to be held back in order to perform surgery on a segment of the intestine. This process can be demanding and typically can require an extra person to hold a conventional retractor. This procedure is even more challenging during minimally invasive surgery (MIS) where a trocar port and surgical technician may be devoted primarily to holding tissue back from the field of view or work area.

SUMMARY

Retraction of items during any surgical or non-surgical procedure moves the items from the field of view or work space. The flexibility and compactness of a retraction device can make it suitable for surgery, especially minimally invasive surgery (MIS). The device can include attachment tools on each end of a line. The attachment tools can allow for attachment of one end of the line to tissue to be moved from the work space. The other end of the line can be attached to non-movable tissue. Alternatively, a loop can be passed through the abdominal wall. Pulling on one end of the line causes the movable tissue to move up and away from the work space. With the cessation of pulling on the line, the tension remains in the device thereby keeping the tissue in place and away from the work area. Elongation of the line can be achieved by using a forceps to pinch the length adjustment mechanism. The safety-release pin mechanism can ensure that tensile force is not applied to tissue above a preset level, which can prevent damage of the tissue. When the upper limit of the tensile force is reached, the two ends of the device will separate, thereby releasing the tension. The safety-release pin can be reloaded and reused.

A flexible netting or adjustable line retractor arrangement can allow for the distribution of force loads over delicate organs or tissue masses during retraction. Atraumatic clips are used to attach the device to non-movable tissue or loops passed through the abdominal wall. Pulling on one end of the line of the adjustable retractor(s) causes the line to shorten and the net to be cinched against the organ of interest. With the cessation of pulling on the line, the tension remains in the line retractor thereby keeping the net cinched against the organ and away from the surgical work area. Elongation of the retractor line is achieved by using a forceps to pinch the release mechanism. The safety-release pin mechanism in the line retractor insures that tensile force or net compressive force is not applied to tissue above a preset level. When the upper limit of force is reached, the two ends of the mechanism will separate, thereby releasing the tension. The safety-release pin can be reloaded during surgery and reused.

In one aspect, an adjustable tissue retractor includes a first tissue attachment tool, a second tissue attachment tool, an adjustable length line connected to the first tissue attachment tool and the second tissue attachment tool, and a length adjuster configured to allow the length of the line to be adjusted unidirectionally to separate tissue and to be selectively released.

In another aspect, an adjustable net retractor includes a sheet, a first adjustable length line connected to the sheet, wherein the first adjustable length line comprises a first tissue attachment tool, and a first length adjuster configured to allow the length of the first adjustable length line to be adjusted unidirectionally to separate tissue and to be selectively released, and a second tissue attachment tool connected to the sheet. The sheet can include a permeable membrane.

In another aspect, a method of retracting tissue includes attaching a first tissue attachment tool to a first location of tissue to be moved away from a second location of tissue, attaching a second tissue attachment tool to a second location of tissue, and adjusting the length of a line connecting the first tissue attachment tool and the second tissue attachment tool to move the first location of tissue relative to the second location of tissue. In another aspect, a method of retracting tissue includes placing a sheet on a tissue to be moved away from a location of tissue, attaching a first tissue attachment tool connected to a first adjustable length line to a first tissue, attaching a second tissue attachment tool connected to the sheet to a second tissue, and adjusting the length of the first adjustable length line connected to the sheet to move the tissue to be moved from the location of tissue. The method can include inserting the first tissue attachment tool into a lumen of a patient. A single operator can adjust the length of the line. The operator can adjust the length of the line with one hand.

In another aspect, an adjustable line retractor includes a line constructed from a flexible material with clips attached at each end and a one-way-pass-through/lock/release mechanism and a maximum-force-limit mechanism attached to the line between the two ends.

In another aspect, a flexible netting includes atraumatic clips at a plurality of locations around a perimeter of a net and an adjustable line retractor at one location on the perimeter.

In various embodiments, one or more of the following features can be employed. T retractor can include a safety-release pin. The adjustable length line can be segmented, partially segmented, or a chain. The length adjuster can include a clamp that moves unidirectionally along the line or selectively unidirectionally along the line. The length adjuster can include a lock configured to secure the line at a fixed length. The clamp can include a release configured to allow the line to extend. The length adjuster can be configured to be operated within a lumen of a patient.

The flexible material can be a non-elastic mono-fiber, a non-elastic-woven filament, or part ball/chain and part non-elastic fiber or non-elastic woven filament. The line can have a grooved surface. The clips at each end of the line can be spring loaded atraumatic alligator type clips, or locking/unlocking non-atraumatic forceps tips. The one-way-pass-through/lock/release mechanism can include a spring loaded cantilevered sharp edged lever within a tube which fits around the line and allows the line to be pulled in one direction but does not permit movement of the line in the other direction unless released by force on the cantilevered lever. The one-way-pass-through/lock/release mechanism can include a single molded tube, with a sharp edge protrusion, which fits around the line and allows the line to be pulled in one direction but does not permit movement of the line in the other direction unless released by force to deform the tube. The maximum-force-limit mechanism can include a small notched pin inserted in a tube with a matching collar and designed to release after a maximum preset force has been applied. The retractor can include a loop for attachment of the line. The net or flexible netting can be shaped, woven from elastic fibers, can include a coiled (elastic) metal wire or can include an elastic sheet or membrane. The net can include square or diamond shaped openings. The adjustable line retractor can include a line constructed from a flexible material that is attached to the net at one end and with a non-traumatic clip attached at the other end and a one-way-pass-through/lock/release mechanism and a maximum-force-limit mechanism attached to the flexible line between the two ends.

In another aspect, a deployable retractor can include a package sized for deployment through a trocar and a retractor as described herein contained within the package.

In another aspect, a method of retracting tissue includes providing a retractor as described herein, and pulling a segment of the line causing the distance between the two ends to shorten. One end of the line can be clipped to an organ and the other end to the abdominal wall. One end can be clipped to an organ and the other end to a loop passed through the abdominal wall. The loop can pass through the abdominal wall and can be secured such that it can not be pulled into a surgical area by the line retractor.

Additional objects, advantages and other novel features of the invention will be set forth in part in the description that follows and in part will become apparent to those skilled in the art upon examination of the foregoing or may be learned with the practice of the invention.

DETAILED DESCRIPTION

Devices for use during surgical or non-surgical procedures can move items from the field of view or work space. Retraction of items during any surgical or non-surgical procedure moves the items from the field of view or work space. The flexibility and compactness of a retraction device can make it suitable for surgery, especially minimally invasive surgery (MIS).

Adjustable retractors can control the position of internal organs, items and the like during surgery or other procedures. The adjustable line retractor can be a flexible line/clip arrangement capable of being attached to two items and shortened, within a pre-set force limit, to reduce the distance between the two items. The adjustable line retractor can include: 1) a flexible line with an atraumatic attachment clip at each end and 2) a one-way-pass-through/lock/release mechanism and a maximum-force-limit release mechanism between the two ends. The device can be used, for example, to retract an internal organ from the field of view during surgery. The flexibility of the adjustable line retractor can allow it to be passed through a trocar and used as an adjustable retractor during minimally invasive surgery. The device can also be used for non-surgical applications. The adjustable net retractor of the invention is a flexible net, with several line retractors around the netting perimeter, which can be used to hold back internal organs or tissue from the field of view during surgery. The adjustable net retractor can include a flexible net and adjustable line retractors which can deliver a distributed force load over the organ or item of interest during retraction. Attached to the perimeter of the flexible net can be several line retractors with atraumatic clips. At least two of the line retractors can be adjustable and contain a one-way-pass-through/lock/release mechanism and a maximum-force-limit release mechanism. The device can allow the netting to be clipped to anchor points on one side and cinched tight by adjustable line retractors clipped to anchor points in other locations. Built-in force limiters can prevent tissue damage when the netting is cinched tight. The flexibility of the adjustable net retractor allows it to be passed through a trocar and used as an adjustable net retractor during minimally invasive surgery. The adjustable net retractor can also be used for non-surgical applications where items can be held out of the field of view or just held in a specific location.

The adjustable line retractor or adjustable net retractor can eliminate the need for an extra person to hold tissue with a conventional retractor during surgery or MIS. A single operator can conduct the surgery and use and adjust the adjustable line retractor or the adjustable net retractor. The operator can use and adjust the adjustable line retractor or the adjustable net retractor using one hand only. In addition, a single entry port can be used for a surgical procedure, simplifying the procedure, reducing cost and reducing risk of complications including infection.

The primary components of an adjustable line retractor can include: an adjustable length line for example a non-elastic line, a length adjuster configured to allow the length of the line to be adjusted unidirectionally such as a one-way-pull through/lock/release mechanism, a safety-release pin or a maximum-force-limit mechanism and two tissue attachment tools such as clips at each end of the adjustable line retractor. The line can be threaded through a one-way-pull through/lock/release mechanism such that one end is available for pulling in order to shorten the retractor and pull an item back from the field of view or work area. With the cessation of pulling, the line can lock in place until the release mechanism is activated. The in-line maximum-force-limit mechanism ensures that tissue will not be damage by excessive force. Should a maximum force, for example two pounds, be exceeded and the safety-release pin released, it can be easily reloaded during a procedure. The features of such a device and its use to control the position of an item, especially in MIS, are new.

Figure 1:
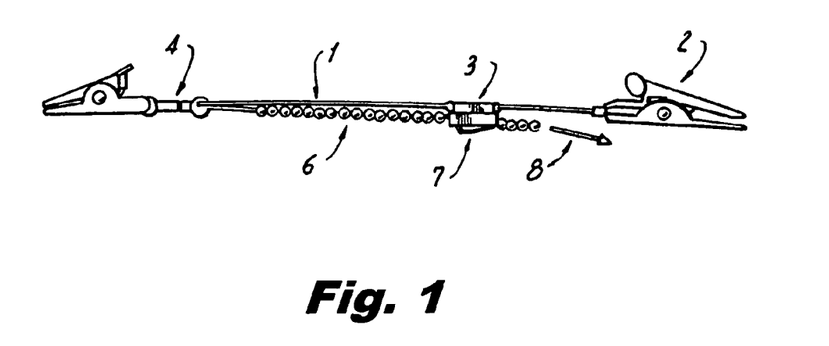
FIG. 1 is a drawing depicting a side view of an adjustable retractor.

Referring to FIG. 1, comprising an adjustable length line constructed from a flexible material, with approximately half made from a woven filament, string or the like and the other half from a ball chain. Tissue attachment tools such as atraumatic grasping clips can be attached at each end and a length adjuster for example a one-way-pass-through/lock/release mechanism is located slightly right of center. The maximum-force-limit mechanism or safety-release pin can be attached to the left clip. The string can be tied to a hole on the right clip, passed through a small channel on top of the one-way-pass-through/lock/release mechanism and knotted at both sides of the channel. The string can then freely pass through the ring on the maximum-force-limit mechanism or safety-release pin located on the left clip. The ball chain part of the line passes through the lower channel of the one-way-pass-through/lock/release mechanism.

Figure 2:
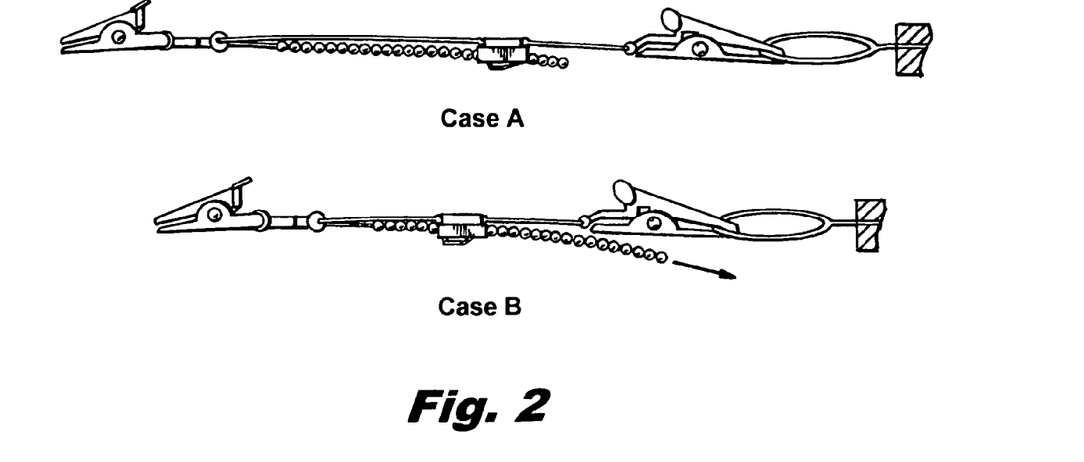
FIG. 2 is a drawing depicting a side view of an adjustable retractor in an initial state (A) and in a partial retracted state (B).
Figure 5:
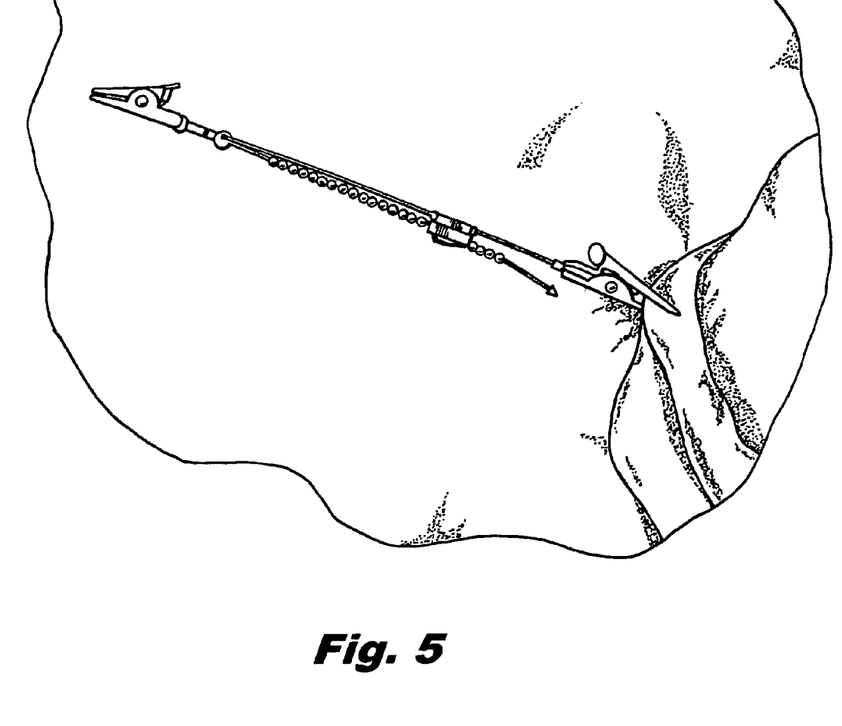
FIG. 5 is a drawing depicting application of an adjustable retractor retracting tissue during a surgical procedure.

The adjustable length line of the retractor can be made up of woven filament segment 1 which is tied to a ball chain segment 6. During fabrication, the line can be tied to a hole in the right clip, passed through the top channel of the one-way-pass-through/lock/release mechanism 3, knotted on either side of the channel, and freely passed through the ring on the maximum-force-limit mechanism located on the left clip. The ball chain segment 6 of the line can be passed through the bottom channel of the one-way-pass-through/lock/release mechanism and a larger ball is clipped on the end to prevent the chain from sliding backwards through the lower channel when the release lever 7 is pressed. The larger ball also enables a better grip with forceps when the ball chain is pulled during retraction. The atraumatic clips 2 at each end, can be spring loaded and open when forceps are used to pinch the top and bottom back part of the clip. The upper rear part of the clip can be turned up slightly to minimize slippage of the forceps during squeezing. The atraumatic clips when pinched open, and then closed, can be used to grab tissue, suture loops and the like. With both clips attached to appropriate tissue points, for example, a force 8 applied as shown in FIG. 1 can cause the device to shorten the distance between attachment points, length A to B in FIG. 2. With the cessation of the pull force 8, the ball chain can stay locked in position because of a spring loaded lever/fin which prevents the ball chain from moving. A cartoon of the adjustable line retractor attached to a suture loop at one end and holding back a tissue flap at the other is shown in FIG. 5. Use of forceps to squeeze the lever 7 on mechanism 3 will free the ball chain and allow for small adjustments or overall release of the retractor line. Removal of the retractor requires both clips to be freed from their appropriate attachments.

Figure 3A:
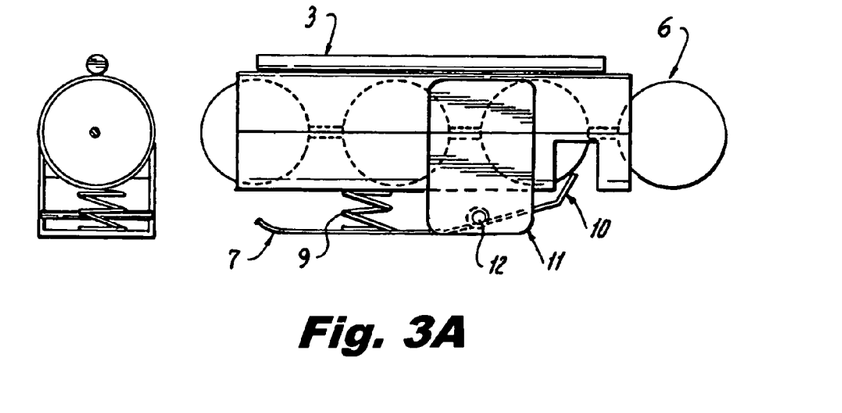
FIG. 3A is a drawing depicting a transparent side and end view of the one-way-pass-through/lock/release mechanism.
Figure 3B:
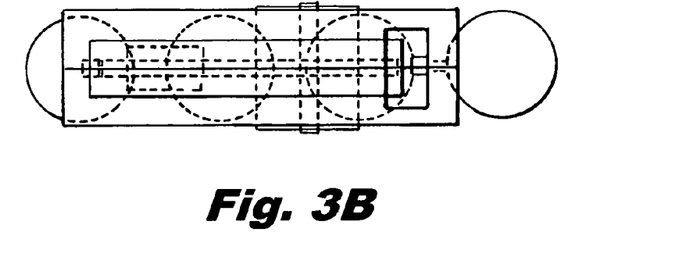
FIG. 3B is a drawing depicting a transparent bottom view of the one-way-pass-through/lock/release mechanism shown in FIG. 3A.

Referring to FIG. 3A, a length adjuster configured to allow the length of the line to be adjusted unidirectionally, for example a one-way-pull through/lock/release mechanism, can be defined by an upper channel for attachment of the line and a lower channel for the one way passage of the ball chain. A spring 9 loaded lever 7 with an angled tip 10 pivots on a pin 12 and allows the ball chain to travel only left to right for shorting the retractor as shown in the FIG. 3A because the curved tip can ride over the balls of the chain in that direction but hinders the ball of the chain from moving in the opposite direction, thereby producing tension in the retractor line once in use. Squeezing of the lever 7 with forceps can allow the balls of the chain to freely move in the opposite direction and reduce the tension in the line of the retractor.

Figure 4:
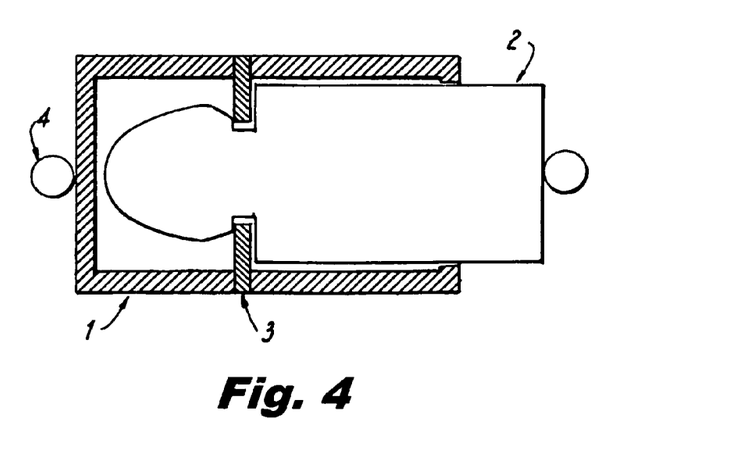
FIG. 4 is a drawing depicting a transparent side view of the maximum-force-limit or safety-release pin mechanism.

The safety-release pin or maximum-force-limit mechanism, FIG. 4, can include a circular tube I in which a pin 2 resides. The pin can have a smooth nose and a circular groove to accept flexible notch studs 3 that will lock in place when the pin is inserted. The notch studs and shape of the groove in the pin can be designed and calibrated to release the pin at a predetermined tension. Circular rings 4 are attached to the ends of the circular tube and pin so that a tissue clip can be attached to the circular tube end and the retractor line can be attached the pin.

Although the adjustable line retractor can be used for any application in which a flap or item needs to be moved or held back from a field of view, including industrial applications, the main focus here is the ability of the adjustable line retractor to pass through a trocar, thereby making it uniquely suitable for minimally invasive surgery.

Figure 6:
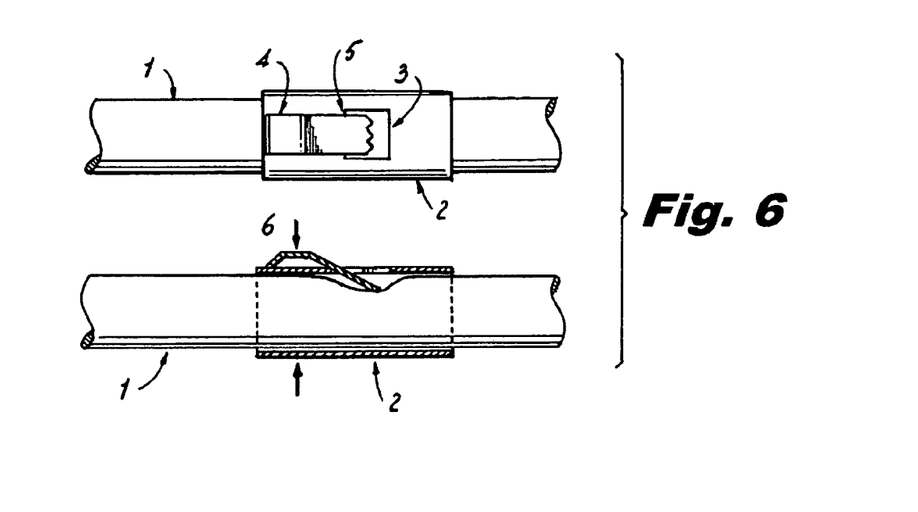
FIG. 6 is a drawing depicting side and top views of a one-way-pass-through/lock/release mechanism.

Another structure for the one-way-pull through/lock/release mechanism is shown in FIG. 6. This structure can include of a polyfilament string 1 which passes through a circular channel 2 that incorporates a rectangular slot 3 through which a spring-loaded-serrated-edged-lever allows the polyfilament string to move from left to right, but not visa versa. The spring loaded lever pivots at the back edge 5 of the slot such that a pinching force 6 on the lever will cause the serrated end to move up thereby releasing the polyfilament and allowing it to move from right to left. As the pinching force is applied the back edge of the lever slides along the surface of the channel, thus no surfaces of discontinuity are available for the lever mechanism to get caught when removing the retractor through a trocar. It should be noted that the polyfilament can be replaced by any material that can withstand the forces of the serrated edges of the level to stop movement in one direction without being severed.

Figure 7:
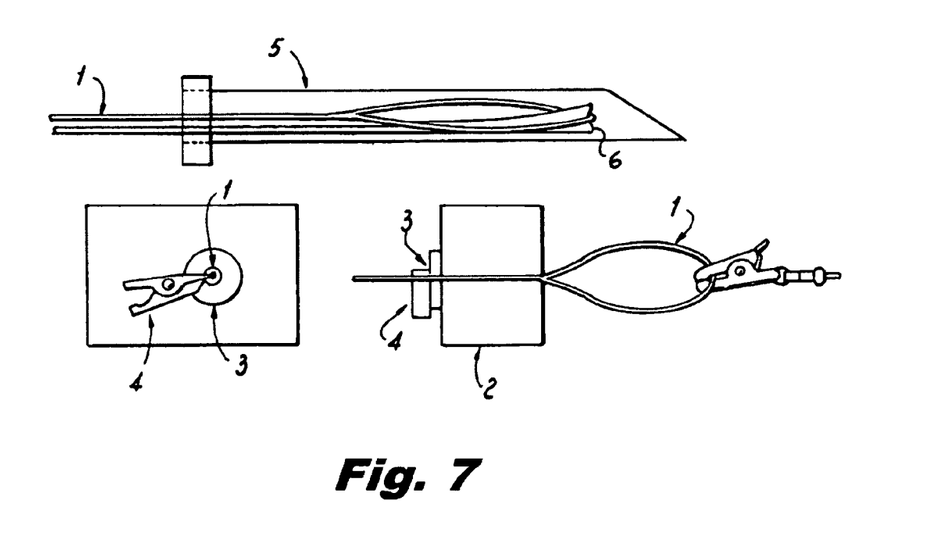
FIG. 7 is a drawing depicting a transparent side view of the anchor loop applier and a front and side view of the anchor loop inserted through simulated abdominal tissue.

The anchor loop, FIG. 7, can include a monofilament 1 (or other filament) with a long tail. The anchor loop can be inserted through the abdominal wall 2, for example, by a thin trocar applicator (top drawing of FIG. 7). The anchor loop is held in place by washer3/clip4 arrangement such that any tension on the anchor loop by the line retractor (see FIG. 6) can be resisted by the washer/clip. The washer distributes the load over the abdominal surface and the clip keeps the monofilament from slipping. The trocar applier includes two major elements: the main trocar barrel 5 with a needle beveled end and a loop holder 6. When the trocar is inserted through the abdominal wall, for example, the loop holder is pushed forward thereby inserting the anchor loop. After the trocar and loop holder are removed the washer/clip is attached to provide a wall anchor for the line retractor.

The primary components of an adjustable net retractor can include: a sheet, for example an elastic netting, at least two tissue attachment tools, for example atraumatic non-adjustable tissue clips, and at least two adjustable line retractors. The two atraumatic non-adjustable clips can be attached around the perimeter of the netting, preferably on two corners. The two adjustable retractors can be located opposite of the two non-adjustable clips. The adjustable line retractor can include a non-elastic line, a one-way-pull through/lock/release mechanism, a maximum-force-limit mechanism and an atraumatic clip at the end not attached to the netting. The non-elastic line can be threaded through the one-way-pull through/lock/release mechanism such that one end is available for pulling thereby causing the line to shorten and the net to be cinched against the organ of interest. With cessation of pulling on the line, the line will lock in place with tension remaining in the line retractor thereby keeping the net cinched against the organ and away from the surgical work area. With the cessation of pulling, the line will stay locked in place until the release mechanism is activated. The in-line maximum-force-limit mechanism assures that tissue or organs will not be damage by excessive tensile or compressive force loads. Should a preset maximum force, for example two pounds, be exceeded and the pin released, it can be easily reloaded during a procedure. The features of such a device and its use to control the position of an item, especially in MIS, are new.

Figure 8:
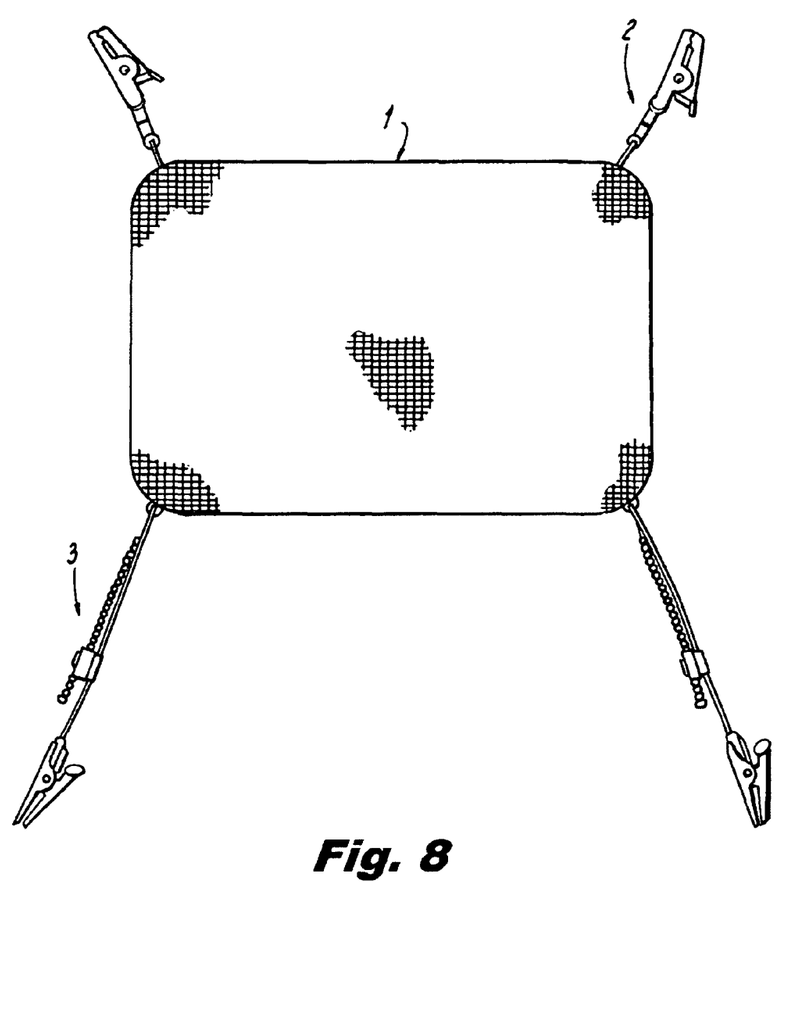
FIG. 8 is a drawing depicting a top view of an adjustable net retractor.
Figure 9A:
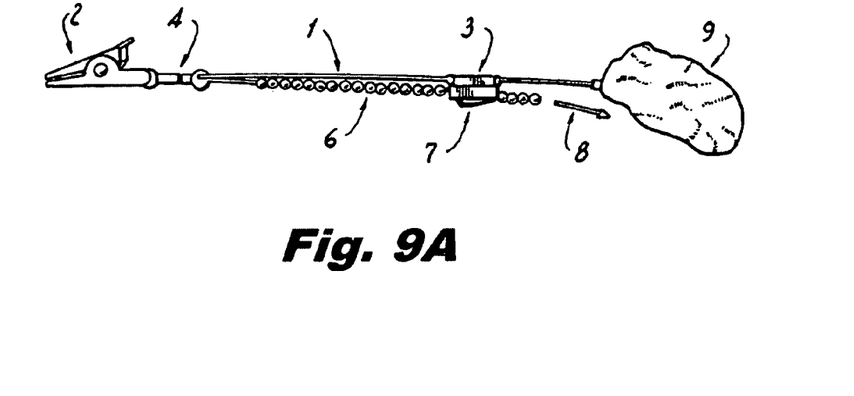
FIG. 9A is a drawing depicting a side view of an adjustable line retractor.
Figure 9B:
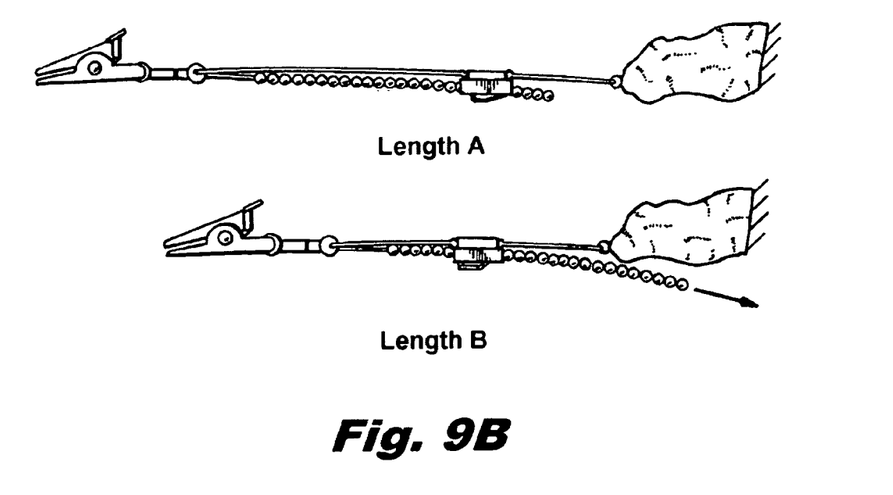
FIG. 9B is a drawing depicting a side view of an adjustable line retractor in the initial state (Length A) and in a partial retracted state (Length B).

The adjustable net retractor is shown in FIGS. 8 and 9. Referring to FIG. 8, an adjustable net retractor can include a sheet, for example an elastic net, which can be shaped, for example, rectangular in shape, with at least two tissue attachment tools for example atraumatic non-adjustable tissue clips and at least two adjustable line retractors. The device can include an elastic net I (which can be rectangular in shape), in FIG. 8, with at least two atraumatic tissue clips 2 on the perimeter at the corners and at least two adjustable line retractors 3 on the perimeter at opposite corners from the non-adjustable retractors. The adjustable line retractor attached to netting 9 is shown in more detail in FIG. 9. The adjustable net retractor can include an adjustable length line, which can be constructed from a flexible material, with approximately half made from a woven filament and the other have from a ball chain. Tissue attachment tools, for example Atraumatic grasping clips, can be attached at one end and a length adjuster, for example a one-way-pass-through/lock/release mechanism is located slightly right of center. The safety-release pin or maximum-force-limit mechanism can be attached to the left clip. The string can be tied to a hole on the right clip, passed through a small channel on top of the one-way-pass-through/lock/release mechanism and knotted at both sides of the channel. The string then freely passes through the ring on the maximum-force-limit mechanism located on the left clip. The ball chain part of the line passes through the lower channel of the one-way-pass-through/lock/release mechanism. The line of the adjustable retractor can be made up of woven filament segment 1, in FIG. 9A which is tied to a ball chain segment 6. During fabrication, the line can be tied to a hole in the right clip, passed through the top channel of the one-way-pass-through/lock/release mechanism 3, knotted on either side of the channel, and freely passed through the ring on the maximum-force-limit mechanism located on the left clip. The ball chain segment 6 of the line is passed through the bottom channel of the one-way-pass-through/lock/release mechanism and a larger ball is clipped on the end to prevent the chain from sliding backwards through the lower channel when the release lever 7 is pressed. The larger ball also enables a better grip with forceps when the ball chain is pulled during retraction. The atraumatic clip 2 at one end, is spring loaded and open when forceps are used to pinch the top and bottom back part of the clip. The upper rear part of the clip is turned up slightly to minimize slippage of the forceps during squeezing. The atraumatic clip when pinched open, and then closed, can be used to grab tissue, suture loops and the like. With the clip attached to appropriate tissue points, for example, a force 8 applied as shown in FIG. 9A can cause the device to shorten the distance between attachment points, length A to B in FIG. 9B. With the cessation of the pull force 8, the ball chain will stay locked in position because of a spring loaded lever/fin which prevents the ball chain from moving. Use of forceps to squeeze the lever 7 on 3 will free the ball chain and allow for small adjustments or overall release of the retractor line.

Figure 10A:
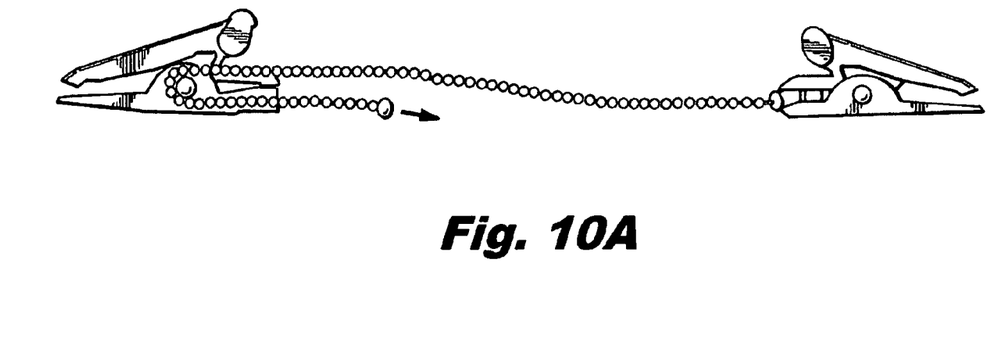
FIG. 10A is a drawing depicting a side view of an adjustable line retractor including a line constructed from a ball chain.

FIG. 10A is a side view of the adjustable line retractor comprising a line constructed from a ball chain. The hold/release mechanism and the safety-release pin may be located in the handles of the tissue clip. The ball and chain can be rotated around the center shaft of the clip providing a larger radius of curvature.

Figure 10B:
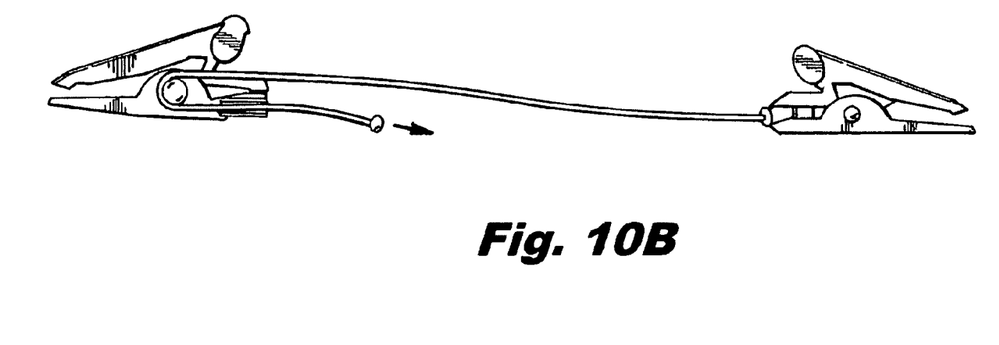
FIG. 10B is a drawing depicting a side view of an adjustable line retractor including a line constructed from a plastic coated twisted wire.

FIG. 10B is a side view of the adjustable line retractor comprising a line constructed from a plastic coated twisted wire. The plastic coated twisted wire allows the teeth in the release mechanism to hold very well.

Figure 11A:
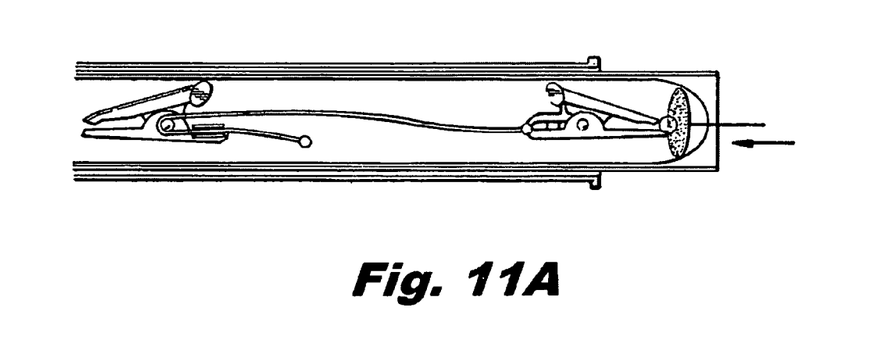
FIGS. 11A, 11B, and 11C are drawings depicting side views of an adjustable line retractor enclosed in a movable sleeve and inserted in a trocar.
Figure 11B:
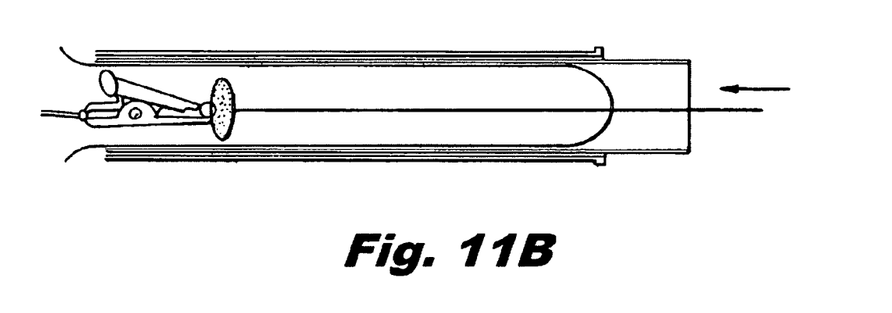
Figure 11C:
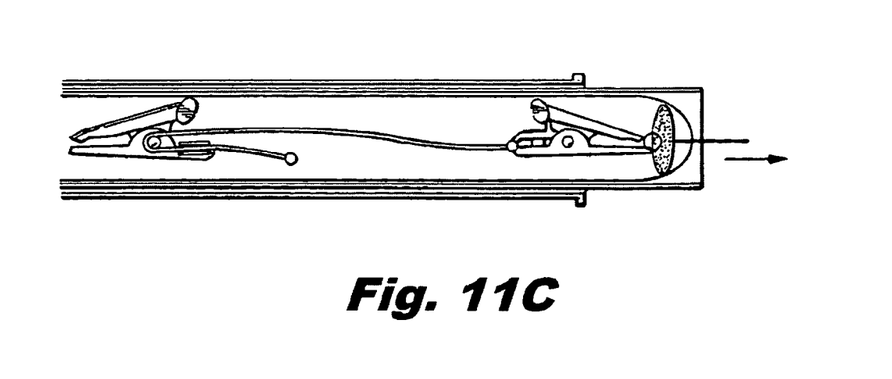

FIGS. 11A, 11B, and 11C are side views of an adjustable line retractor enclosed in a movable sleeve and inserted in a trocar. Either the adjustable line retractor or the adjustable net retractor may have a thin flexible sleeve around them for ease of passing through a trocar for introducing or retrieving units. The sleeve can be designed to flare to ensure smooth introduction of the line retractor in the trocar. A plunger allows introducing or pulling the line retractor in or out of the trocar.

Figure 12:
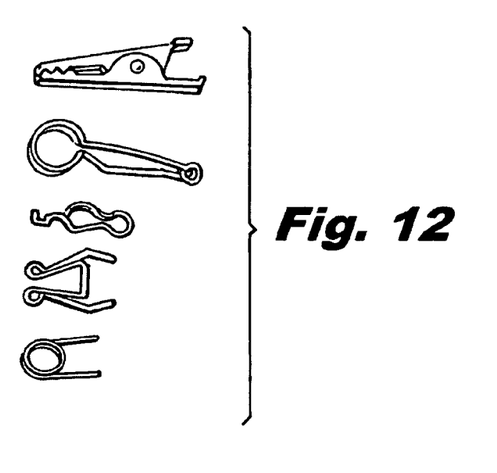
FIG. 12 shows various tissue attachment tools.

FIG. 12 shows various tissue attachment tools that can be used. The tissue attachment tools may be of various styles and tips. For general purposes, standard alligator type clips may suffice with torque springs and tips lined with a tooth/groove configuration designed to grasp the material during the retracting process without producing damage. Other clip designs may include a low profile concave-convex jaw design, parallel sided jaw design or clips configured to have tips with tissue contacting surfaces to mimic any style of surgical graspers.

For surgical applications, the entire device must be made of materials that can be sterilized. In addition, the entire assembly must be capable of being prepackaged, sterile, in a suitable container.

Other embodiments are within the scope of the following claims.

What is claimed is:

1. A method of retracting tissue comprising:
    a) attaching a first tissue attachment tool to a first location of tissue to be moved toward a second location of tissue;
    b) attaching a second tissue attachment tool to said second location of tissue;
    c) adjusting the length of a line connecting the first tissue attachment tool and the second tissue attachment tool to move the first location of tissue relative to the second location of tissue; and
    d) attaching a one-way-pass-through/lock/release mechanism to the line between the first and second tissue attachment tools.

2. The method of claim 1, further comprising inserting the first tissue attachment tool into a lumen of a patient.

3. The method of claim 1, wherein a single operator adjusts the length of the line.

4. The method of claim 3, wherein the operator adjusts the length of the line with one hand.

5. A method of retracting tissue comprising:
    a) providing an adjustable line retractor including a line constructed from a flexible material with clips attached at each end and a one-way-pass-through/lock/release mechanism and a maximum-force-limit mechanism attached to the line between the two ends; and
    b) pulling a segment of the line causing the distance between the two ends to shorten, wherein one end of the line is clipped to an organ and the other end to the abdominal wall.

6. A method of retracting tissue comprising:
a) providing an adjustable line retractor including a line constructed from a flexible material with clips attached at each end and a one-way-pass-through/lock/release mechanism and a maximum-force-limit mechanism attached to the line between the two ends; and
b) pulling a segment of the line causing the distance between the two ends to shorten, wherein one end is clipped to an organ and the other end to a loop passed through the abdominal wall.

7. The method of claim 6, wherein the loop passes through the abdominal wall and is secured such that it can not be pulled into a surgical area by the line retractor.

\* \* \* \* \*